(12) United States Patent
Timmons

(10) Patent No.: US 8,226,621 B2
(45) Date of Patent: Jul. 24, 2012

(54) URINE COLLECTION BAG SUPPORT BELT

(76) Inventor: Vicki C. Timmons, Chambersburg, PA (US)

( * ) Notice: Subject to any disclaimer, the term of this patent is extended or adjusted under 35 U.S.C. 154(b) by 235 days.

(21) Appl. No.: 12/452,515

(22) PCT Filed: Jul. 31, 2008

(86) PCT No.: PCT/US2008/009211
§ 371 (c)(1),
(2), (4) Date: Jan. 6, 2010

(87) PCT Pub. No.: WO2009/017761
PCT Pub. Date: Feb. 5, 2009

(65) Prior Publication Data
US 2010/0121288 A1 May 13, 2010

Related U.S. Application Data

(60) Provisional application No. 60/962,702, filed on Aug. 1, 2007.

(51) Int. Cl.
*A61M 1/00* (2006.01)
*A61F 5/44* (2006.01)

(52) U.S. Cl. ......... 604/327; 604/331; 604/343; 604/345

(58) Field of Classification Search ................... 604/327, 604/343, 345, 331
See application file for complete search history.

(56) References Cited

U.S. PATENT DOCUMENTS

| | | | |
|---|---|---|---|
| 1,382,446 A * | 6/1921 | Warren | 2/311 |
| 1,857,179 A * | 5/1932 | Bowman | 604/345 |
| 2,612,895 A | 10/1952 | Magee | |
| 4,029,103 A | 6/1977 | McConnell | |
| 4,122,851 A * | 10/1978 | Grossner | 604/347 |
| 4,511,358 A | 4/1985 | Johnston, Jr. et al. | |
| 4,976,698 A | 12/1990 | Stokley | |
| 5,026,362 A | 6/1991 | Willett | |
| 5,032,118 A | 7/1991 | Mason | |
| 5,271,745 A * | 12/1993 | Fentress et al. | 604/179 |
| 5,336,195 A * | 8/1994 | Daneshvar | 604/179 |
| 5,468,229 A * | 11/1995 | Chandler | 604/179 |
| 5,496,282 A * | 3/1996 | Militzer et al. | 604/179 |
| 5,643,233 A | 7/1997 | Turner | |
| 5,716,344 A * | 2/1998 | Kiel | 604/174 |
| 5,728,070 A * | 3/1998 | Walker et al. | 604/179 |
| 5,776,105 A * | 7/1998 | Corn | 604/174 |
| 5,836,497 A * | 11/1998 | Pelish | 224/677 |
| 5,935,116 A | 8/1999 | Kristensen | |
| 6,129,709 A * | 10/2000 | Millen | 604/179 |
| 6,270,485 B1 * | 8/2001 | Ekey | 604/345 |
| 6,273,872 B1 * | 8/2001 | Friedman | 604/174 |

(Continued)

*Primary Examiner* — Tatyana Zalukaeva
*Assistant Examiner* — Ginger T Chapman
(74) *Attorney, Agent, or Firm* — Richard C. Litman

(57) ABSTRACT

The urine collection bag support belt (10) supports urine bags (B) beneath clothing or when sleeping. The support (10) includes a waist cincture (12) having opposed first and second ends (18, 20) and a central portion. At least one releasable fastener (14, 16) is provided for releasably securing the first end (18) to the second end (20) in order to secure the cincture (12) to the waist. At least one strap (22) is attached to the central portion of the belt (12) and extends downward. The strap (22) is adapted for releasably supporting the urine bag (B). In addition, at least one elongated strip is secured to the belt (12) that supports the tubing (T) connected to the urine collection bag (B) by retaining a serpentine portion of the tubing (T) against the waist cincture (12).

13 Claims, 4 Drawing Sheets

U.S. PATENT DOCUMENTS

| | | |
|---|---|---|
| 6,296,164 B1 * | 10/2001 | Russo .......................... 224/602 |
| 6,471,680 B1 | 10/2002 | Cawood |
| 6,544,232 B1 * | 4/2003 | McDaniel .................... 604/174 |
| 6,565,546 B1 | 5/2003 | Hurst |
| 6,599,278 B1 | 7/2003 | Nichols |
| 6,610,032 B1 * | 8/2003 | Prody .......................... 604/179 |
| 6,887,223 B2 * | 5/2005 | Bisbee ......................... 604/353 |
| D508,994 S | 8/2005 | Hostetler |
| 7,895,673 B2 * | 3/2011 | Forselius et al. ................ 2/237 |
| 7,927,311 B1 * | 4/2011 | Bachelder .................... 604/179 |
| 2005/0075615 A1 | 4/2005 | Bonham |
| 2005/0256466 A1 | 11/2005 | Winkler |

\* cited by examiner ical Field

The present invention relates to devices for supporting medical implants, and particularly to a urine collection bag support belt for supporting a urine collection bag and related tubing, especially the type of bag and tubing used by patients who have undergone a nephrostomy.

BACKGROUND ART

A nephrostomy is a procedure that inserts a tube into the renal pelvis in order to divert the flow of urine from the kidney out through the skin. A nephrostomy may be resorted to in cases of trauma or certain diseases, such as cancer. Since there is no longer sphincter control over the flow of urine, the patient must wear and learn to manage an artificial device for the collection of urine. Typically urine is collected in a bag or pouch.

The patient must support the tubing an collection bag beneath his or her clothing and when sleeping. The patient may feel physically uncomfortable from supporting the weight of the tubing and bag, experience local irritation and skin deterioration if urine comes into contact for prolonged periods, and be subject to lower self-esteem concerning his or her body image.

The necessary tubing and bags are typically secured to the patient by surgical tape and/or rubber straps. However, such tape often causes the wearer irritation on the skin, and removal of the tape may be damaging to the user's skin, particularly around the opening formed through the user's skin adjacent the kidneys. As the bag fills, the bag gets progressively heavier, and it becomes more difficult (and less comfortable) for the tape to support the bag. Thus, a urine collection bag support belt solving the aforementioned problems is desired.

DISCLOSURE OF THE INVENTION

The urine collection bag support belt is a belt for holding a urine collection bag and supporting the attached tubing, particularly in patients who have undergone a nephrostomy. The support for a urine collection bag includes a belt adapted to be worn about the waist of a user, with the belt having opposed first and second ends and a central portion.

At least one releasable fastener is provided for securing the first end of the belt to the second end thereof. The at least one fastener may be, for example, hook and loop type fasteners attached to the respective first and second ends of the belt.

Further, at least one strap is attached to the central portion of the belt and extends downward therefrom. The strap is adapted for releasably supporting the urine collection bag. Preferably, at least one releasable fastener is provided for releasably attaching the strap(s) to the urine collection bag. The releasable fastener may be, for example, hook and loop fasteners attached to the strap(s). Preferably, a pair of straps are provided, each strap being attached to the belt adjacent a respective one of the first and second ends thereof.

In addition, a portion of the collection bag tubing is releasably secured to the belt, preferably by at least one elongated strip secured to the belt. The at least one elongated strip is adapted for at least partially covering the portion of tubing and releasably securing the portion of tubing against the belt. At least one releasable fastener is provided for releasably attaching the at least one elongated strip to the belt. Preferably, a pair of such strips are provided.

Further, the belt is preferably adjustable in length. The central portion of the belt is adapted to be folded in order to selectively adjust the length thereof, and a clip is preferably provided for clipping the folded material of the central portion in place.

These and other features of the present invention will become readily apparent upon further review of the following specification and drawings.

BRIEF DESCRIPTION OF THE DRAWINGS

Similar reference characters denote corresponding features consistently throughout the attached drawings.

BEST MODES FOR CARRYING OUT THE INVENTION

Figure 1:
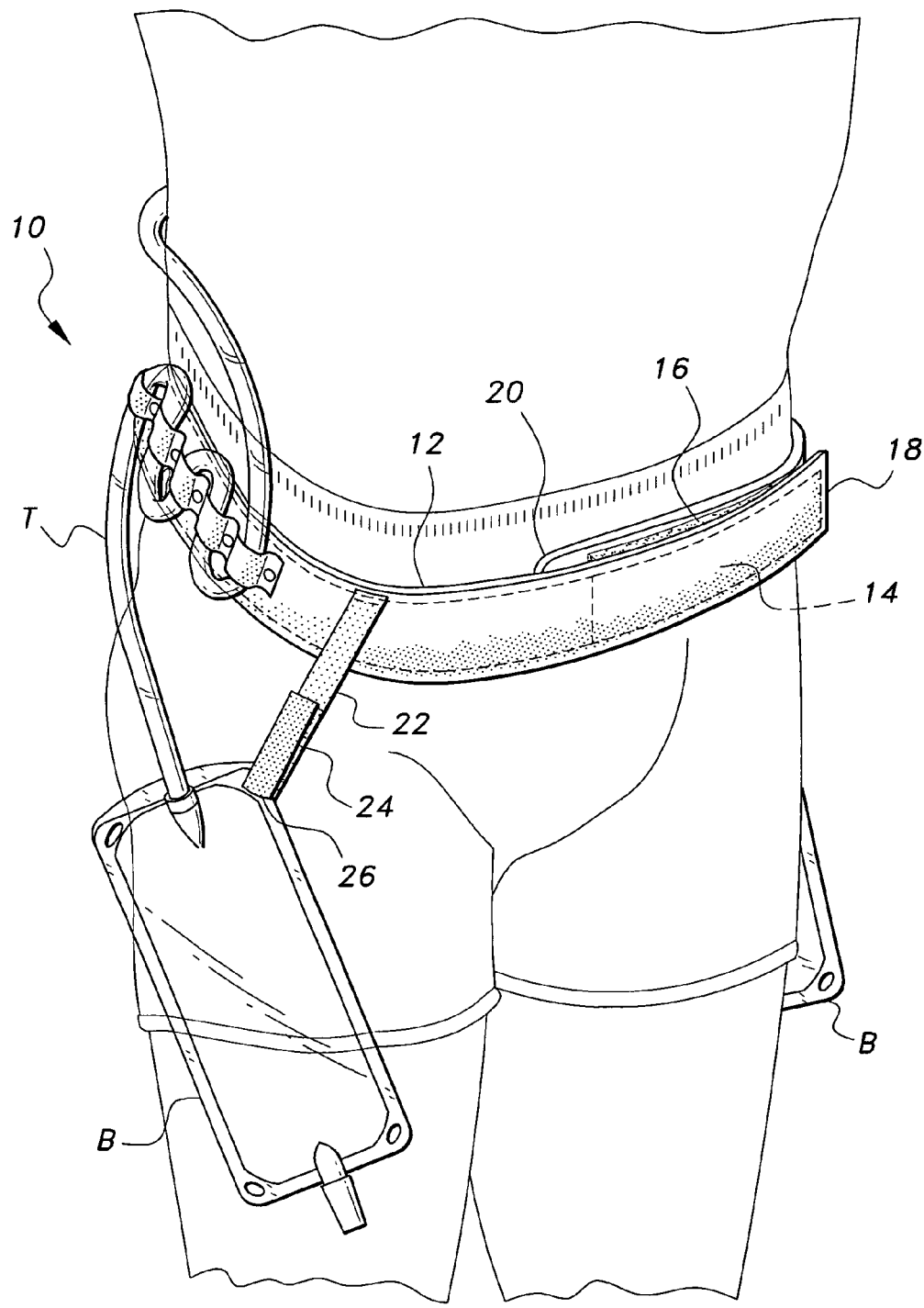
FIG. 1 is a front, environmental, perspective view of a urine collection bag support belt according to the present invention.
Figure 2:
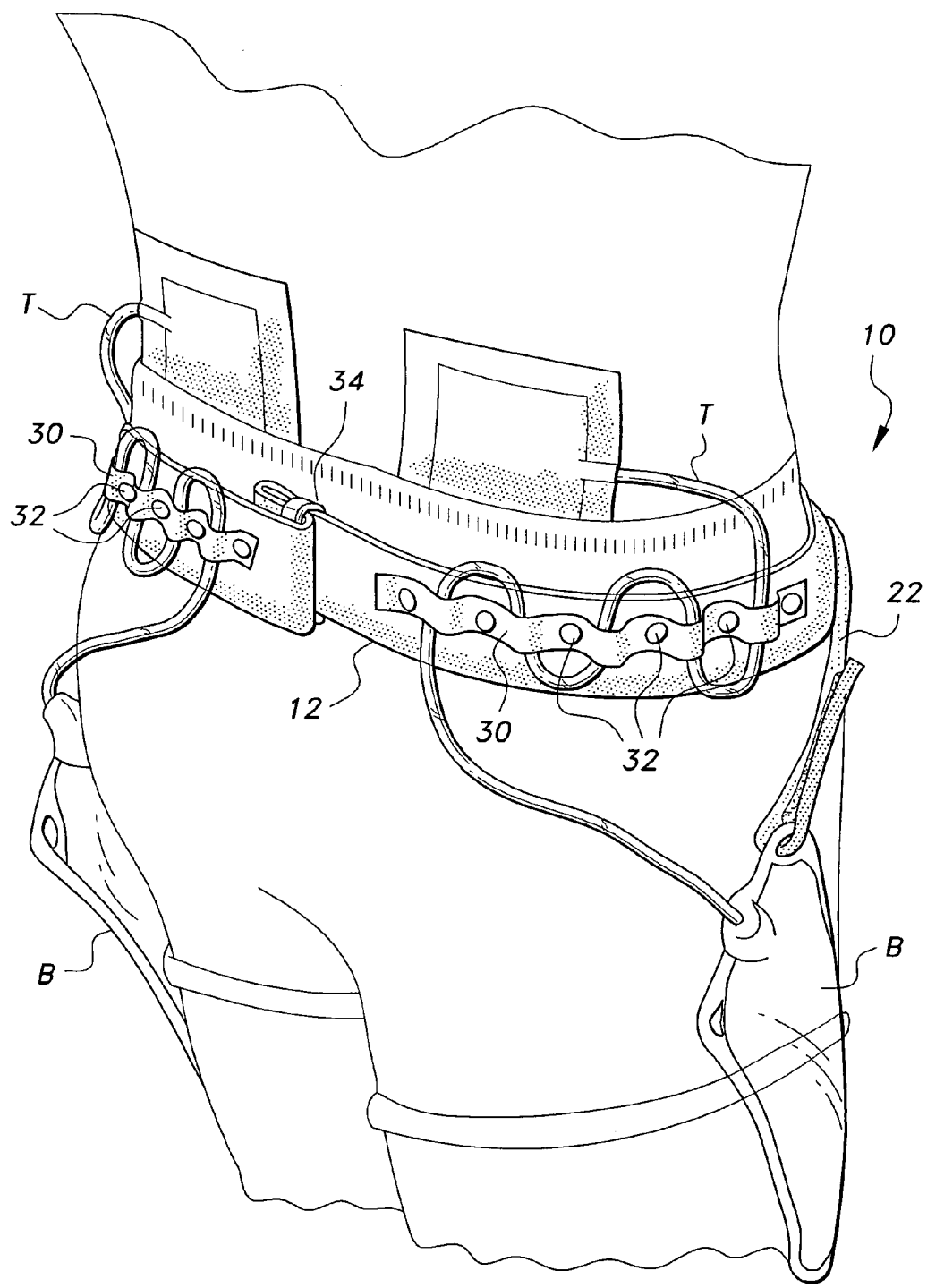
FIG. 2 is a rear, environmental, perspective view of the urine collection bag support belt according to the present invention.

The present invention is directed towards a urine collection bag support belt 10. As best shown in FIGS. 1 and 2, the belt 10 supports a urine collection bag B and tubing T connected to the bag B. Such bags are often used by patients who have undergone a nephrostomy.

Figure 3:
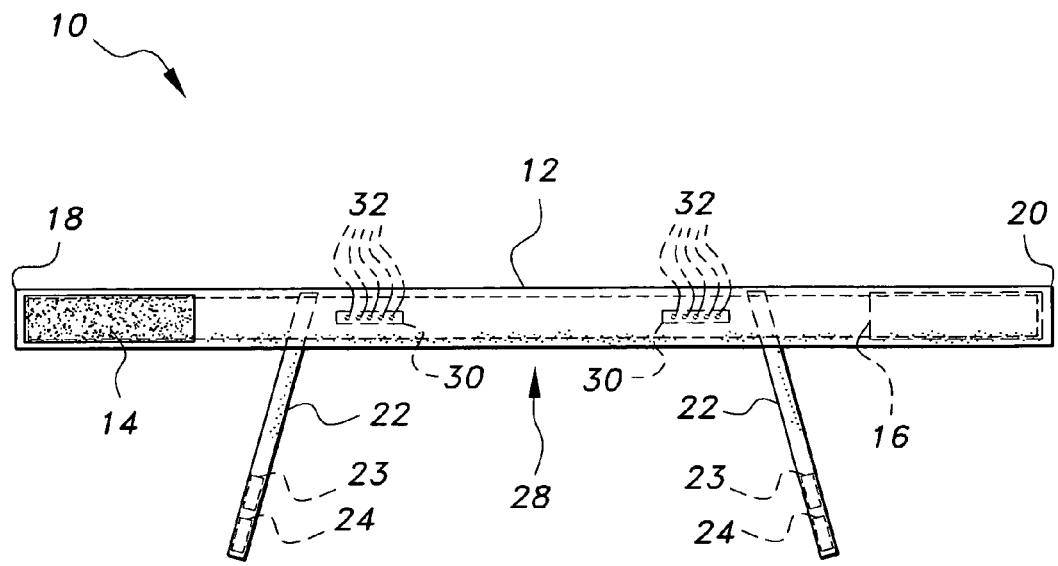
FIG. 3 is a bottom view of the urine collection bag support belt according to the present invention.
Figure 4:
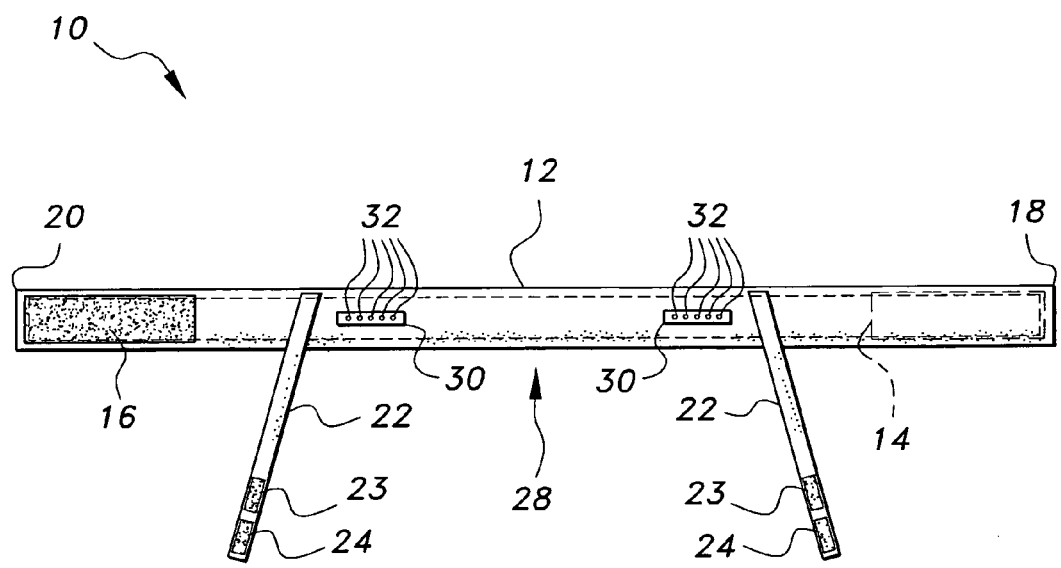
FIG. 4 is a top view of the urine collection bag support belt according to the present invention.

The belt 10 includes a waist cincture 12 adapted to be worn about the waist of a user, as shown, with the cincture 12 having opposed first and second ends 18, 20 (as best shown in FIGS. 3 and 4) and a central portion 28 extending between the opposing ends 18, 20. Cincture 12 is preferably formed from a fabric material selected for both comfort and strength in supporting bag B. The fabric is preferably washable and durable, and may incorporate elastic therein, similar to a typical undergarment.

At least one releasable fastener is provided for securing the first end 18 of the cincture 12 to the second end 20 thereof. The at least one fastener may be, for example, mating hook and loop fasteners 14, 16 attached to the respective first and second ends 18, 20 of the cincture 12, as best shown in FIGS. 3 and 4. It should be understood that any suitable type of releasable fastener may be used.

Further, at least one strap 22 is secured to the central portion 28 of the cincture 12 and extends downward therefrom. The strap 22 is adapted for releasably supporting the urine collection bag B. Preferably, at least one releasable fastener is provided for releasably securing the at least one strap 22 to the urine collection bag B. The strap fastener may be, for example, mating hook and loop fasteners 23, 24 attached to the strap 22, as best shown in FIGS. 3 and 4. It should be understood that any suitable type of releasable fastener may be used. Preferably, a pair of straps 22 are provided, as shown, each strap 22 being attached to the cincture 12 adjacent a respective one of the first and second ends 18, 20 thereof. As best illustrated in FIG. 2, nephrostomies often result in drainage of urine from both kidneys, thus requiring a pair of urine bags. When so equipped, the pair of straps 22 may be arranged symmetrically on cincture 12 for supporting a respective pair of bags B.

In addition, a portion of tubing T connected to the urine collection bag B is releasably secured to the cincture 12, preferably by at least one elongated strip 30 attached to the cincture 12. The strip 30 is adapted for at least partially covering the portion of tubing T and releasably securing the portion of tubing T against the cincture 12. At least one releasable fastener is provided for releasably attaching the strip 30 to the cincture 12, such as the snap-type fasteners 32 shown in the drawings. It will be noted that strip 30 extends parallel to cincture 12, and that snap fasteners 32 are spaced apart on the strip 30 an the cincture 12 in such a manner that strip 30 forms loops adapted for securing a sinuous portion of the tubing T to the cincture, thereby distributing the load formed by urine filling the bag B and relieving stress and discomfort that might otherwise be referred to the point where tubing T exits the skin. Preferably, a pair of such tubing support strips 30 are provided, allowing for the retention of a pair of tubing portions, one for each of the pair of bags B. It should be understood that any suitable releasable fastener may be utilized for releasably securing the tubing T to cincture 12.

Figure 5:
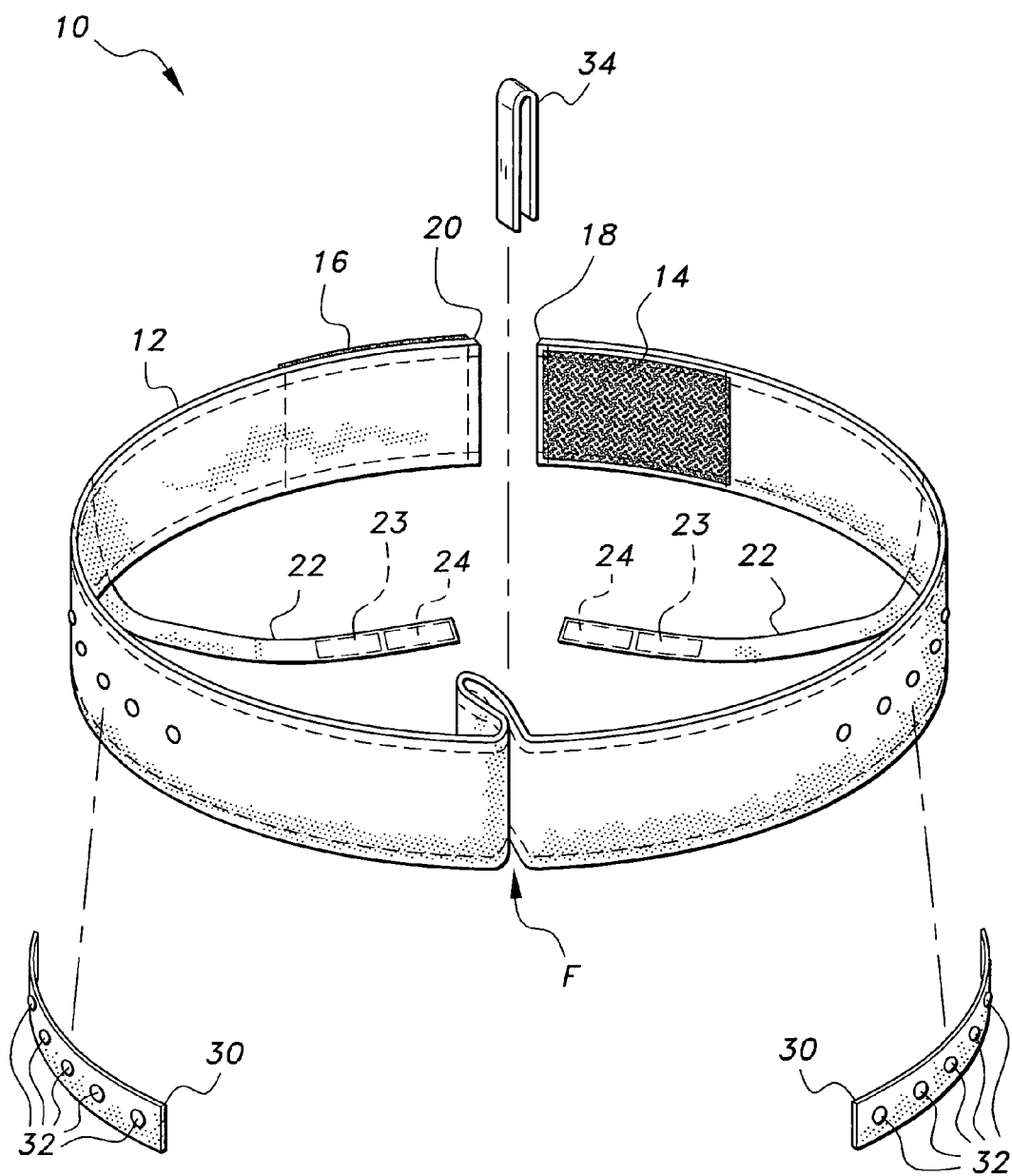
FIG. 5 is an exploded perspective view of the urine collection bag support belt according to the present invention.

Further, the cincture 12 is preferably adjustable in length. As shown in FIGS. 2 and 5, the central portion 28 of the cincture 12 is adapted to be folded (indicated in FIG. 5 by fold F) in order to selectively adjust the length thereof, and a clip 34 is preferably provided for releasably clipping the folded material of the central portion 28 in place.

In use, the cincture 12 is secured about the waist of the user through engagement of hook and loop fasteners 14, 16 on first and second ends 18, 20. The length of the cincture 12 may be adjusted to fit securely about the user's waist by folding the central portion 28 and securing the fold F with clip 34. Tubing T is then wound through, and secured by, snaps 32 of strips 30, and bags B are secured by straps 22. Typical urine bags, such as exemplary bags B, include openings for receiving straps, and straps 22 are threaded through these openings for supporting bags B. Straps 22 are secured to bags B by engagement of hook and loop fasteners 23, 24. The belt 10 may then be worn comfortably under the user's clothing, and bags B may be removed, as necessary, through disengagement of hook and loop fasteners 23, 24 of straps 22, and disengagement of snaps 32 of strips 30 to free tubing T.

It is to be understood that the present invention is not limited to the embodiments described above, but encompasses any and all embodiments within the scope of the following claims.

The invention claimed is:

1. A urine collection bag support belt, comprising:
a waist cincture adapted to be worn about the waist of the user, the cincture having opposed first and second ends and a central portion extending between the opposed ends, wherein the central portion is foldable to selectively adjust the length of the cincture;
means for releasably maintaining the folded central portion in the selected adjusted length;
a cincture fastener releasably securing the first end of the cincture to the second end thereof;
at least one bag-supporting strap extending downward from the central portion of the cincture, the strap being adapted for releasably supporting a urine collection bag; and
at least one tube-supporting strip disposed on the central portion of the cincture, the strip forming spaced apart loops on the central portion of the cincture adapted for supporting tubing connected to the urine collection bag when the tubing is folded in serpentine manner.

2. The urine collection bag support belt as recited in claim 1, wherein said cincture fastener comprises hook and loop fasteners attached to the opposing ends of the cincture.

3. The urine collection bag support belt as recited in claim 1, further comprising a releasable strap fastener attached to said bag supporting strap adapted for releasably securing said at least one bag-supporting strap to the urine collection bag.

4. The urine collection bag support belt as recited in claim 3, where said strap fastener comprises mating hook and loop fasteners.

5. The urine collection bag support belt as recited in claim 1, wherein said at least one bag-supporting strap comprises a pair of straps, each strap being secured to said belt adjacent a respective one of said first and second ends thereof.

6. The urine collection bag support belt as recited in claim 1, further comprising a plurality of mating releasable fasteners attached to said strip and to said cincture for forming the loops.

7. The urine collection bag support belt as recited in claim 6, wherein said plurality of mating releasable fasteners comprises mating snap fasteners.

8. The urine collection bag support belt as recited in claim 1, wherein said tube-supporting strip extends parallel to said cincture.

9. The urine collection bag support belt as recited in claim 1, wherein said at least one tube-supporting strip comprises a pair of elongated strips.

10. The urine collection bag support belt as recited in claim 1, wherein said means for selectively adjusting the length of said cincture comprising a clip releasably attachable to the folded central portion of said cincture.

11. A urine collection bag support belt, comprising:
an elongated waist cincture adapted to be worn about the waist of the user, the cincture having opposed first and second ends and a central portion extending between the opposed ends;
a cincture fastener releasably securing the first end of the cincture to the second end thereof;
at least one bag-supporting strap extending downward from the central portion of the cincture, the strap being adapted for releasably supporting a urine collection bag; and
a plurality of tube-supporting strips disposed on spaced apart locations on the central portion of the cincture, each of the strips extend parallel to the cincture, a plurality of strip fasteners being located at spaced apart regions of the strip thereby forming a plurality of spaced apart loops opening in a direction transverse to the elongate axis of the cincture and being adapted for supporting tubing connected to the urine collection bag when the tubing is folded in serpentine manner in and out of the loops.

12. The urine collection bag support belt as recited in claim 11, wherein the strip fasteners forming the plurality of loops are releasable fasteners.

13. The urine collection bag support belt as recited in claim 12, wherein the releasable strip fasteners comprise mating snap fasteners.

* * * * *